United States Patent
Breitruck et al.

(10) Patent No.: US 11,116,932 B2
(45) Date of Patent: *Sep. 14, 2021

(54) EXPIRATORY VALVE

(71) Applicant: HAMILTON MEDICAL AG, Bonaduz (CH)

(72) Inventors: Felix Breitruck, Buchs SG (CH); Dino De-Stefani, Chur (CH)

(73) Assignee: HAMILTON MEDICAL AG, Bonaduz (CH)

(*) Notice: Subject to any disclaimer, the term of this patent is extended or adjusted under 35 U.S.C. 154(b) by 198 days.

This patent is subject to a terminal disclaimer.

(21) Appl. No.: 15/804,113

(22) Filed: Nov. 6, 2017

(65) Prior Publication Data
US 2018/0126113 A1 May 10, 2018

(30) Foreign Application Priority Data
Nov. 8, 2016 (DE) ...................... 10 2016 121 379.9

(51) Int. Cl.
*A61M 16/20* (2006.01)
*F16K 15/14* (2006.01)

(52) U.S. Cl.
CPC ........ *A61M 16/208* (2013.01); *A61M 16/206* (2014.02); *F16K 15/144* (2013.01); *A61M 2205/42* (2013.01); *A61M 2207/00* (2013.01); *A61M 2209/084* (2013.01)

(58) Field of Classification Search
CPC ............ A61M 16/208; A61M 16/0009; A61M 16/20; A61M 16/201; A61M 16/202; A61M 16/203; A61M 16/205; A61M 16/206; A61M 16/207; A61M 16/209; A61M 2205/42; F16K 15/00; F16K 15/14; F16K 15/144; F16K 27/0236; A62B 18/10; Y10T 137/891
See application file for complete search history.

(56) References Cited

U.S. PATENT DOCUMENTS 4,241,756 A * 12/1980 Bennett ................. A61M 16/20
                                                             137/496
4,630,604 A    12/1986 Montesi
5,020,532 A     6/1991 Mahoney et al.
(Continued)

FOREIGN PATENT DOCUMENTS

GB          2036263 A    6/1980
JP       S55-107167 A    8/1980
(Continued)

OTHER PUBLICATIONS

Hamilton Medical AG, "Hamilton G5 Service Manual", May 2007 (Year: 2007).*
(Continued)

*Primary Examiner* — Bradley H Philips
*Assistant Examiner* — Savannah L Gabriel
(74) *Attorney, Agent, or Firm* — Rothwell, Figg, Ernst & Manbeck, P.C.

(57) ABSTRACT

An expiratory valve (10) of a ventilation device (100) is provided, including a valve body (12) having a fluid inlet (14) and a fluid outlet (16) for breathing air of a patient formed therein. The valve body (12) has at least one reinforcing rib (36, 38) formed around the fluid inlet (14).

20 Claims, 3 Drawing Sheets

(56) References Cited

U.S. PATENT DOCUMENTS

| | | | |
|---|---|---|---|
| 7,066,177 B2* | 6/2006 | Pittaway | A61M 16/20 128/201.28 |
| 2005/0033239 A1* | 2/2005 | Argentine | A61M 39/0606 604/167.04 |
| 2006/0131535 A1* | 6/2006 | Mendl | F01L 3/10 251/337 |
| 2007/0012360 A1 | 1/2007 | Flynn | |
| 2009/0071478 A1* | 3/2009 | Kalfon | A61M 16/0051 128/204.17 |
| 2009/0293878 A1 | 12/2009 | Tatarek | |
| 2013/0048124 A1* | 2/2013 | Huang | A61M 16/208 137/843 |
| 2015/0205307 A1* | 7/2015 | McNeely | F16K 31/1266 137/489 |

FOREIGN PATENT DOCUMENTS

| | | |
|---|---|---|
| JP | H06-504922 A | 6/1994 |
| JP | 2004-522487 A | 7/2004 |
| JP | 2004-532707 A | 10/2004 |
| JP | 2014-133172 A | 7/2014 |
| WO | 00/045883 A1 | 8/2000 |

OTHER PUBLICATIONS

Nanomold Coating, "5 Major Advantages to Using Plastic Injection Molding for the Manufacturing of Parts", Sep. 11, 2014 (Year: 2014).*

Hamilton Medical AG, "GALILEO Service Manual", Oct. 31, 2005 (Year: 2005).*

Reprocessing guide per EN ISO 17664 (English), Expiratory Valve Set Reprocessing Guide, Hamilton Medical, 15 pages, Jun. 28, 2017.

German Search Report cited in 10 2016 121 379.9 dated Jun. 28, 2017, 8 pgs.

Office Action issued for Japanese Patent Application No. 2017-214478 dated May 10, 2021, 10 pages.

Office Action issued for Japanese Patent Application No. 2017-214480 dated May 10, 2021, 5 pages.

* cited by examiner

EXPIRATORY VALVE

CROSS REFERENCE TO RELATED APPLICATIONS

This application claims the benefit of German Patent Application No. 10 2016 121 379.9 filed on Nov. 8, 2016, the disclosure of which is incorporated herein in its entirety by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

The present invention relates to an expiratory valve of a ventilation device, comprising a valve body having a fluid inlet and a fluid outlet for breathing air of a patient formed therein, the valve body having at least one reinforcing rib formed around the fluid inlet.

This expiratory valve is used in a ventilation device for mechanical ventilation of patients. The present invention also relates to such a ventilation device.

BACKGROUND OF THE INVENTION

Field of the Invention

In mechanical ventilation, breathing air is supplied to a patient in a mechanical manner, as a rule under positive pressure. Mechanical ventilation can support or completely replace the patient's own breathing. Supply of the ventilation air takes place in successive ventilation cycles. Each ventilation cycle comprises an inspiration phase followed by an expiration phase. The ventilation air is supplied during the inspiration phase of a respective ventilation cycle, as a rule mechanically or in any case in device-assisted manner and at a positive pressure with respect to the pressure prevailing in the patient's airways. Expiration takes place during a subsequent expiration phase of the ventilation cycle. As a rule, there is no positive pressure or negative pressure applied to the airways in the expiration phase. Rather, expiration is to take place passively by relaxing the airways with respect to ambient pressure, in which patient's own expiratory efforts are to be supported as much as possible. Expiration of the breathing air and discharge of the breathing air to the environment is to be effected with the aid of the expiratory valve described herein. The expiratory valve is arranged in the ventilation system in a conduit for exhaled air, as a rule at the downstream end of this conduit. On its side facing away from the patient, there is usually ambient pressure prevailing. When a positive pressure with respect to this pressure is applied to the valve during an expiration phase from the side of the patient, the expiratory valve is to open and permit discharge of the exhaled air to the environment. In doing so, the expiratory valve is to reliably recognize the beginning and the end of expiration phases and react accordingly. To this end, there is used a valve membrane which, depending on whether a sufficiently high positive pressure with respect to its side facing the environment is present on its side facing the airways, opens or closes a fluid passage between the airways and the environment.

DESCRIPTION OF RELATED ART INCLUDING INFORMATION DISCLOSED UNDER 37 CFR 1.97 AND 1.98

In the past, there was frequently the problem arising that the expiration valve caused unpleasantly loud noise during operation. In some cases, it could even be observed that oscillating pressure fluctuations in the exhaled air were caused or increased by the expiratory valve, which in the end led to malfunctions in ventilation. In the case of this phenomenon known as auto trigger or auto cycle, pressure fluctuations caused by, or increased by, the expiratory valve are erroneously detected by the ventilation device as the end of the expiration phase, and the ventilation device prematurely initiates the next inspiration phase. This is very unpleasant for the mechanically ventilated patient and may even lead to danger for the mechanically ventilated patient. The expiratory valve according to the invention is intended to avoid or at least reduce such problems.

BRIEF SUMMARY OF THE INVENTION

In comparison with the expiratory valves used so far, the expiratory valve according to the invention, as set out in the initial paragraphs of this disclosure, permits improved guiding of the exhaled air. In particular, the expiratory valve is more sensitive in reacting to the beginning and the end of the expiration phase, and the generation of noise during operation of the expiratory valve is clearly suppressed. Moreover, it is possible to better control the phenomenon of auto trigger or auto cycle.

The expiratory valve is designed such that breathing air during exhalation, i.e. during the expiration phase, may enter the expiratory valve by way of the now open fluid inlet, in particular may enter a valve plenum enclosed by the expiratory valve. During the inspiration phase, the fluid inlet is preferably closed.

The fluid outlet is designed such that exhaled breathing air can be discharged to an environment.

It is suggested to provide the valve body with at least one stiffening or reinforcing rib formed around the fluid inlet. The valve body may be provided in particular with a plurality of reinforcing ribs formed around the fluid inlet. The plurality of reinforcing ribs may be arranged in succession, in particular in specific intervals from each other, around a circumference of the fluid inlet. A single reinforcing rib, for example, may be designed as a solid body surrounding the fluid inlet at least partially. The at least one reinforcing rib is formed in particular on a side of the valve body facing away from the fluid flow path so that it does not interfere with the fluid flow between the fluid inlet and the fluid outlet. The reinforcing rib(s) are located in particular on a lower side of the valve body and are formed for example on the lower side of a valve bottom forming the bottom of the valve body, on a side of the valve bottom facing away from the fluid flow path.

The reinforcing rib or ribs are suitable to stiffen or reinforce the valve bottom. This has a particularly advantageous effect in a bulging portion surrounding the fluid inlet. Such a bulging portion can form a groove or channel extending around the fluid inlet, as will still be described in more detail in the following. The provision of reinforcing rib(s) at the valve body leads to an increase in the second moment of area of the valve body, in particular the valve bottom, across the cross-sectional area of the fluid flow path. The valve body becomes more torsion-resistant in this region, so that the fluid flow entering the valve plenum and flowing along the fluid flow path induces lesser vibrations of the valve body, especially the valve bottom. This inhibits above all the generation of noise, but also causes much lesser retroactive pressure effects that become felt in the breathing air conduit connected to the fluid inlet. The problem of an erroneous detection of the end of an expiration cycle and thus effected auto trigger or auto cycle processes in the ventilation device can thus be suppressed significantly.

The valve body can be made in particular of plastics material. For example, it is expedient to produce the valve body in an injection-molding process. The valve body then is an injection-molded part. For example, the valve body together with the valve bottom can be made from a plastics material suitable for injection-molding, such as polyethylene, polypropylene or another thermoplastic plastics material.

It is advantageous to form the at least one reinforcing rib integrally with the valve body. The term integral is to be understood to the effect that the at least one reinforcing rib and the valve body are manufactured as one component part, for example, that the at least one reinforcing rib is produced in the same injection-molding process as the valve body, in particular as a single-component injection-molded part.

The at least one reinforcing rib may advantageously extend outwardly with respect to an edge of the fluid inlet. The expression outwardly is to designate the direction of the at least one reinforcing rib, which is arranged such that it reinforces the portion of the valve bottom between the edge of the fluid inlet and the outer edge of the valve bottom as efficiently as possible. In particular, the at least one reinforcing rib thus extends along a course that is transverse to a fluid flow path extending around the fluid inlet. In particular, the at least one reinforcing rib may extend in the radial direction with respect to a center of a cross-sectional area of the fluid inlet. However, it is also conceivable that the at least one reinforcing rib does not extend exactly in the radial direction, but in addition extends in the circumferential direction, for example spirally towards the outer edge of the valve bottom. The at least one reinforcing rib in particular may be arranged outside of the edge of the fluid inlet.

In embodiments, the valve body defines a cup-shaped valve plenum which, at least in part, is enclosed on its lower side by the valve body, in particular by a valve bottom formed by the valve body and optionally by an outer edge originating from the valve bottom and constituted by the valve body as well, and into which the fluid inlet opens. On the top side thereof, the valve plenum may be confined by a valve membrane constituting a cover. The valve plenum defines a cavity which may have fluid (exhaled breathing air) applied thereto via the fluid inlet and from which the fluid (exhaled breathing air) can be discharged via the fluid outlet. In particular, the valve plenum has the fluid flow path formed therein between the fluid inlet and the fluid outlet. In particular, the valve plenum is at least partially confined by the valve bottom on its lower side, and the fluid inlet opens into the valve bottom. The valve bottom may extend in particular in a dish-like manner between the fluid inlet and an outer edge of the valve body (in particular, the valve plenum), with the outer edge of the valve bottom at the same time constituting the outer edge of the valve body. The term "dish-like" is to point out that the valve bottom, apart from a possible channel-like recess around the fluid inlet still to be described in more detail, extends in a substantially flat or flat conical manner between the fluid inlet and an outer edge. The fluid inlet then is formed in particular in a central part of the valve bottom. The fluid inlet may have in particular a circular cross-sectional area with an also circular fluid entry surface.

Certain embodiments may be formed such that the valve bottom bulges in an axial direction in a portion around the fluid inlet. The wording "bulges in an axial direction" is to point out that the valve bottom has a convex configuration at least in a section including a fluid inlet axis, namely in a portion located between the edge of the fluid inlet and the outer edge of the valve bottom. Convex means that, in such a sectional view, a line connecting two points on the valve bottom extends through the valve plenum. The valve bottom accordingly forms a groove or channel extending around the fluid inlet, with the bottom of said channel bulging in an axial direction between the edge of the fluid inlet and the outer edge of the valve bottom. In contrast to this, the valve bottom of expiratory valves presently in use has a flat conical configuration, i.e. it does not form a bulge or protuberance.

The at least one reinforcing rib is suited to reinforce the valve bottom in the bulging portion. Generation of noise when breathing air flows can thus be reduced, as vibrations of the valve bottom are suppressed.

The at least one reinforcing rib may comprise at least one first reinforcing rib and at least one second reinforcing rib. The at least one first reinforcing rib is an inner reinforcing rib that is arranged radially inside of the at least one second reinforcing rib. Accordingly, the at least one second reinforcing rib is an outer reinforcing rib. The at least one first reinforcing rib in particular extends from the edge of the fluid inlet along the valve bottom towards the outside. The at least one second reinforcing rib extends in particular from an outer edge of the valve bottom along the valve bottom towards the inside. The at least one first reinforcing rib extends in particular between the edge of the fluid inlet and the bulging portion of the valve bottom. The at least one second reinforcing rib extends in particular between the bulging portion of the valve bottom and an outer edge of the valve bottom. In particular, the at least one second reinforcing rib terminates in a flange-like shoulder formed at the outer edge of the valve bottom. The shoulder may have, for example, at least one step extending around the edge of the valve bottom, preferably at least two spaced apart steps, with the at least one second reinforcing rib merging into the step or an inner one of the steps, respectively.

The valve bottom in particular may originate from an edge of the fluid inlet defining a fluid entry surface. There is no step created between the fluid entry surface and the valve bottom. In this manner, there are avoided sharp-edged boundaries of the fluid inlet with respect to the valve plenum. This enhances the formation of an as quiet as possible flow of the fluid into the expiratory valve as well as through the expiratory valve during the expiration phase. In the case of known expiratory valves, the fluid inlet in contrast projects into the valve plenum, in particular the fluid inlet projects a certain distance beyond the valve bottom. The valve bottom then does not originate from the edge of the fluid inlet defining the fluid entry surface, and the fluid flow passes a step when flowing into the valve plenum, which enhances the formation of turbulence and stalls or air stream separation of the fluid flow flowing into the expiratory valve.

For reducing the generation of noise and retroactive pressure effects, it may also be expedient when the valve plenum has an aerodynamically efficient design in terms of flow along the fluid flow path between the fluid inlet and the fluid outlet. The aerodynamically efficient design of the valve plenum, in particular, of the fluid flow path, may be enhanced in particular when the valve bottom, starting from an inside of the fluid inlet at the edge of the fluid entry surface, has a rounded contour on its side facing the valve plenum. The fluid flow entering the valve plenum from the fluid inlet thus reaches the fluid flow path in a substantially non-swirling manner and without stalls, and flows towards the fluid outlet. This results in a reduction of operating noise when the fluid outlet is opened. Moreover, retroactive pressure effects into the breathing air conduit connected to the fluid inlet are effectively suppressed, so that the risk of erroneous detections of an end of the expiration phase by the ventilation device is reduced.

The flow-optimized design of the valve plenum, in particular such that only rounded contours are formed along the fluid flow path in the valve plenum from fluid inlet to fluid outlet, is considered to constitute a subject matter of the present invention that is independently worth protecting. The applicant reserves the right to claim independent protection for this, independently of the presence of one or more reinforcing ribs formed around the fluid inlet. Moreover, the aforementioned design of a valve bottom that bulges in an axial direction in a portion around the fluid inlet may also contribute in achieving a flow-optimized design.

In certain embodiments, the fluid flow path may have a cross-sectional area expanding towards the fluid outlet. In this design, the fluid flow path is particularly well matched to the volume flow, which increases towards the fluid outlet, of the fluid (the exhaled air) flowing during expiration through the expiratory valve, which is opened in this phase. The larger the volume flow, the larger the cross-sectional area available in the fluid flow path. In particular, partial volumes of the fluid flow path with respect to angular portions of equal size each change along a circumference of the fluid inlet, such that these partial volumes increase in the direction towards the fluid outlet. This reduces the formation of turbulence and disturbances in the fluid flow and provides the possibility that the expiratory valve can react to changes in the flow of exhaled air in the airways in a much more reliable, but at the same time also a more sensitive manner. Retroactive pressure effects, which in conventional expiratory valves often led to the aforementioned auto trigger malfunctions, occur far less.

The cross-sectional area of the fluid flow path is to be understood as being the area of the space available for the fluid flow in cross-sectional areas transverse to, in particular orthogonal to, the main direction of the fluid flow between the fluid inlet and the fluid outlet when the expiratory valve is opened.

In particular, the design may be such that the axial bulge or protuberance has a depth that varies around the circumference of the fluid inlet. The depth of the bulge can be defined as a distance, measured in an axial direction, between the valve bottom at the edge of the fluid inlet and the valve bottom at the deepest location of the bulge along a section from the edge of the fluid inlet to the outer edge of the valve bottom. In particular, the depth of the bulge is to increase in the circumferential direction towards the fluid outlet. Thus, partial volumes of the bulge, with respect to angular portions of equal size each, change along the circumference of the fluid inlet, such that these partial volumes increase in size in the direction towards the fluid outlet. In certain embodiments, the depth of the bulge in the circumferential direction may be smallest on a side opposite the fluid outlet, and in the circumferential direction may be largest on the side located towards the fluid outlet.

As mentioned hereinbefore, the fluid inlet may be arranged in particular in a central portion of the valve plenum. The fluid outlet may be arranged at a further outward location with respect to the fluid inlet, in particular further outside in the radial direction, in particular at an outer edge of the valve plenum. In the case of such a design, the cross-sectional area of the fluid flow path between the fluid inlet and the fluid outlet presents itself in each case as the area of the valve plenum in a respective radial section from the fluid inlet axis to the outer edge of the valve plenum.

In certain embodiments, the valve body may have a fluid inlet portion having the fluid inlet formed therein. In particular, the fluid inlet portion may be formed integrally with the valve body, and thus may be formed as an injection-molded part in the event that the valve body is an injection-molded part. The fluid inlet portion in particular may extend from the valve bottom, in particular from a lower side of the valve bottom. The fluid inlet portion may extend e.g. orthogonally with respect to the valve bottom. The fluid inlet axis designates an imaginary line in the longitudinal direction of the fluid inlet portion, which is arranged centrally with respect to the fluid inlet portion. With the fluid entry surface being orthogonal to the fluid inlet, the fluid inlet axis is orthogonal to the fluid entry surface defined by the fluid inlet and is arranged centrally with respect to the fluid entry surface. In certain embodiments, the fluid inlet portion may define a first pin-like protrusion which may be designed for connection of a breathing air tube. For example, the first pin-like protrusion may have a cylindrical or conical shape, and in particular may be designed as a cylindrical or conical pipe fitting having the fluid inlet formed therein. The fluid inlet in particular may have a circular cross-sectional area.

Moreover, the valve body in particular may define a fluid outlet portion having the fluid outlet formed therein. The fluid outlet portion in particular may have a second pin-like protrusion. The fluid outlet portion in particular may be formed integrally with the valve body, for example in the form of an injection-molded part as well. The second pin-like protrusion in particular may have a cylindrical or conical shape. If desired, the second pin-like protrusion may be formed, for example, as a cylindrical or conical pipe fitting having the fluid outlet formed therein. However, the second protrusion often will open directly into the environment. The fluid outlet in particular may have a circular cross-sectional area.

The bulging portion of the valve bottom, which defines the fluid flow path between the fluid inlet and the fluid outlet, may merge into the fluid outlet portion. The bulging portion of the valve bottom in particular may merge into a sidewall of the fluid outlet portion. In particular, the groove or channel defined by the bulging valve bottom has a maximum depth at the transition to the fluid outlet portion.

As in the case of the fluid inlet portion, also the fluid outlet portion in particular may extend away from the valve bottom, in particular from a lower side of the valve bottom. The fluid inlet portion may extend orthogonally with respect to the valve bottom.

Furthermore, it is advantageous when the valve body has a support on the top side of which a valve membrane can be placed with an abutment area formed at the outer edge of the same, with the support having an uneven design on its top side.

As described hereinbefore, the expiratory valve comprises furthermore a valve membrane associated with the fluid inlet, which can be displaced at least between a position closing the fluid inlet and a position opening the fluid inlet. The valve membrane may be designed without a drive of its own, so that it can be displaced between the closing position and the opening position merely by pressure differences between its side facing the fluid inlet and its side facing away from the fluid inlet. In addition or as an alternative, however, there may also be provided an actuator displacing the valve membrane in a reciprocating manner between the closing position and the opening position. This actuator preferably is driven by the ventilation device. This valve membrane has its abutment area, which is formed at the outer edge of the same, resting on the top side of the support. The expiratory valve in particular comprises furthermore a clamping member, for example, a clamping ring, cooperating with the valve body in such a manner that the clamping member establishes clamping engagement with the valve membrane. By way of this clamping engagement, which is effected in particular at the outer periphery of the valve membrane by clamping engagement with the clamping member, the valve membrane is fixed to the valve body. In this regard, the valve membrane can be fixed to the valve body by the clamping member in such a manner that, when a positive pressure is present on its side associated with the fluid inlet as compared to its side associated with the valve plenum, the valve membrane can be brought into a position opening the fluid inlet with respect to the valve plenum. As long as this is not the case, in particular with equal pressures or a negative pressure on its side associated with the fluid inlet as compared to its side associated with the valve plenum, the valve membrane remains in a position closing the fluid inlet with respect to the valve plenum.

The present invention in addition relates to a ventilation device comprising an expiratory valve of the type described hereinbefore, which can be connected to an expiration air conduit.

BRIEF DESCRIPTION OF THE SEVERAL VIEWS OF THE DRAWING(S)

The invention will be explained in more detail in the following by way of an embodiment with reference to the drawings, wherein.

DETAILED DESCRIPTION OF THE INVENTION

For like or functionally alike components, the same reference numerals will be used in all of the figures. A detailed description of such components will be given in each case for the first figure only which shows the respective reference numeral. It is to be understood that the same description also applies to all other figures in which the component bearing the same reference numeral is shown, unless pointed out specifically to the contrary.

Figure 1:
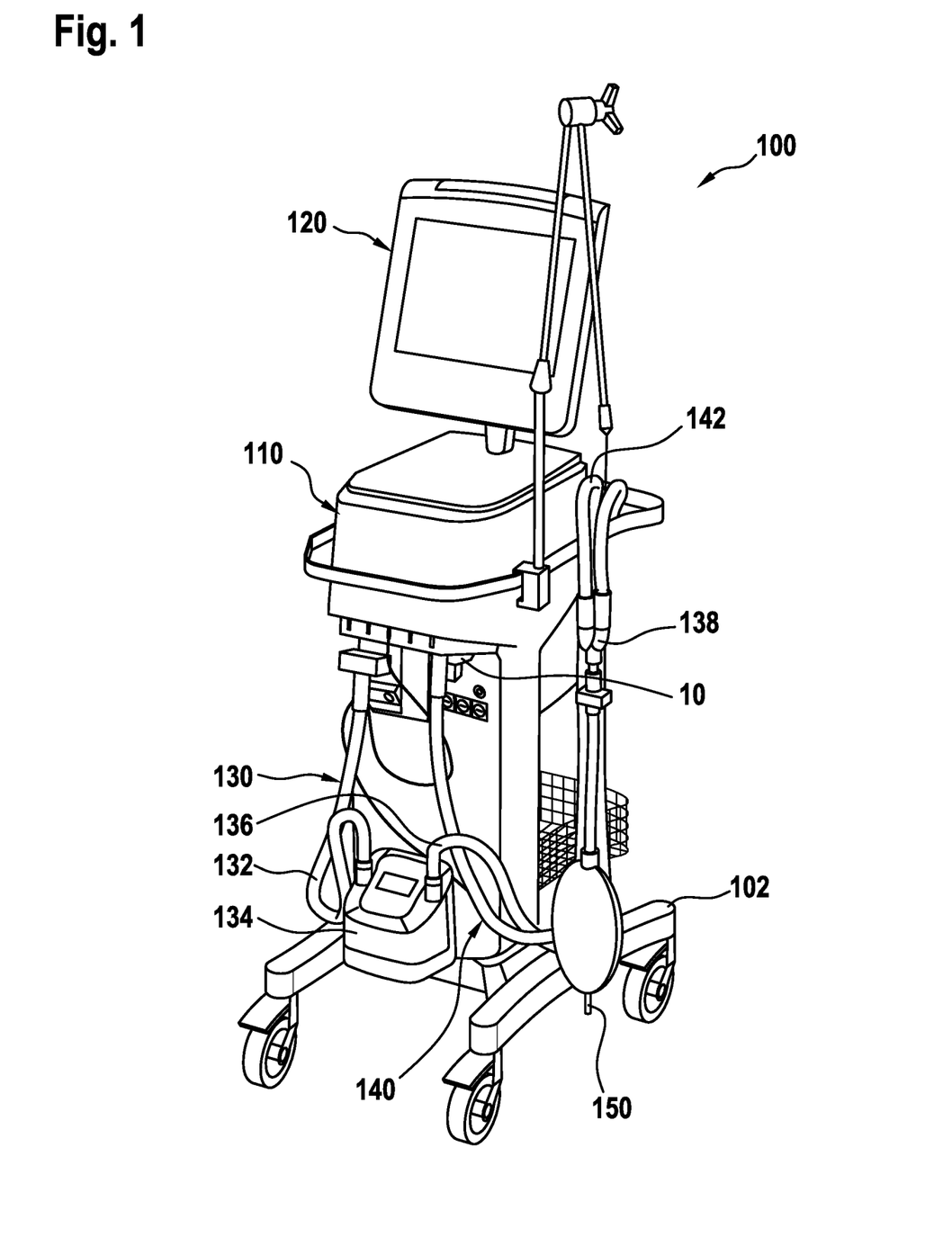
FIG. 1 shows a ventilation device for mechanical ventilation of patients, comprising a control unit, a monitor as well as tubes for supplied breathing air and for exhaled air.

FIG. 1 shows a ventilation device 100 for mechanical ventilation of patients. The ventilation device 100 comprises a rack 102 that is movable on rollers, along with a control unit 110 and a monitor 120 as well as a conduit 130 for ventilation air supplied by the device and a conduit 140 for exhaled air. The conduit 130 for supplied ventilation air comprises a first ventilation air tube 132 extending from the control unit 110 to a humidification unit 134 where the ventilation air is passed through a water reservoir. From the humidification unit 134, a second ventilation air tube 136 extends to a T-piece 138. From the T-piece, the ventilation air provided by the ventilation device 100 during an inspiration phase of the ventilation cycle is supplied to the patient via a conduit 150. Via conduit 150, the air exhaled by the patient during an expiration phase of the ventilation cycle is also returned to the ventilation device 100. To this end, an additional breathing air tube 142, belonging to conduit 140 for exhaled air, branches off from the T-piece 138. The breathing air tube 142 leads to an expiratory valve, generally designated 10, which will be explained in more detail in the following with reference to FIGS. 2 to 4.

Figure 2:
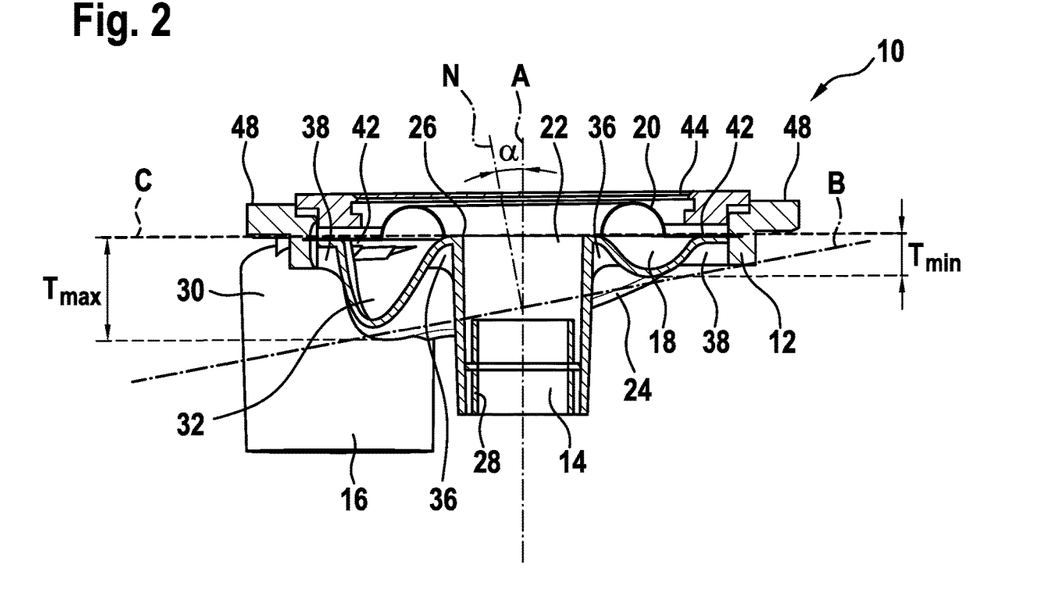
FIG. 2 shows a sectional view of an expiratory valve according to an embodiment.
Figure 3:
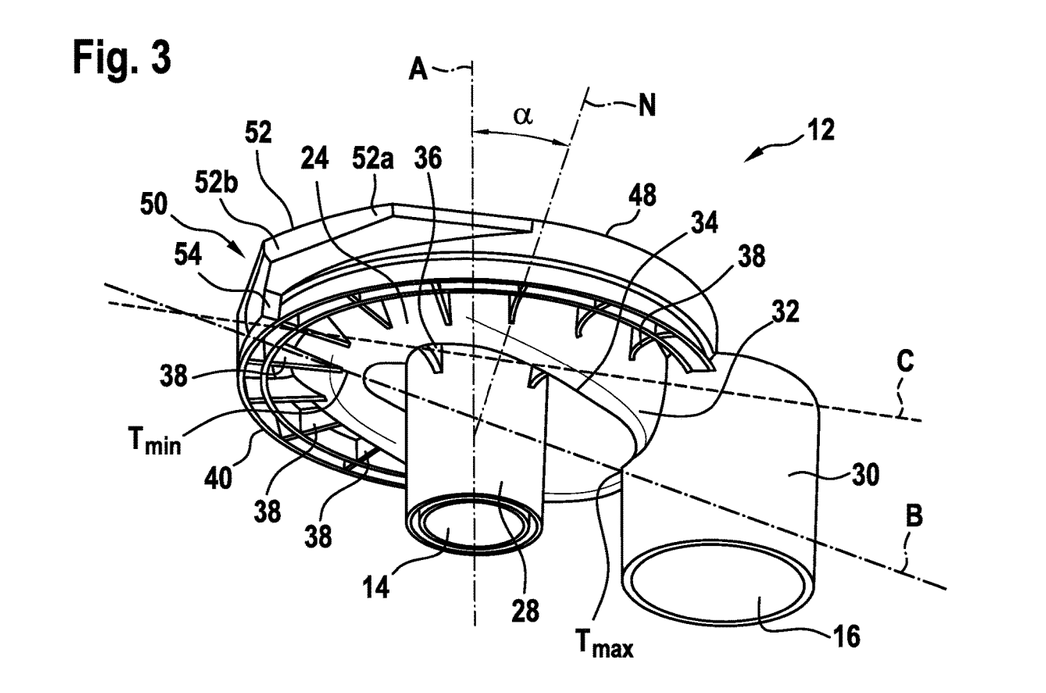
FIG. 3 shows a perspective view of the valve body of the expiratory valve of FIG. 2 from below.
Figure 4:
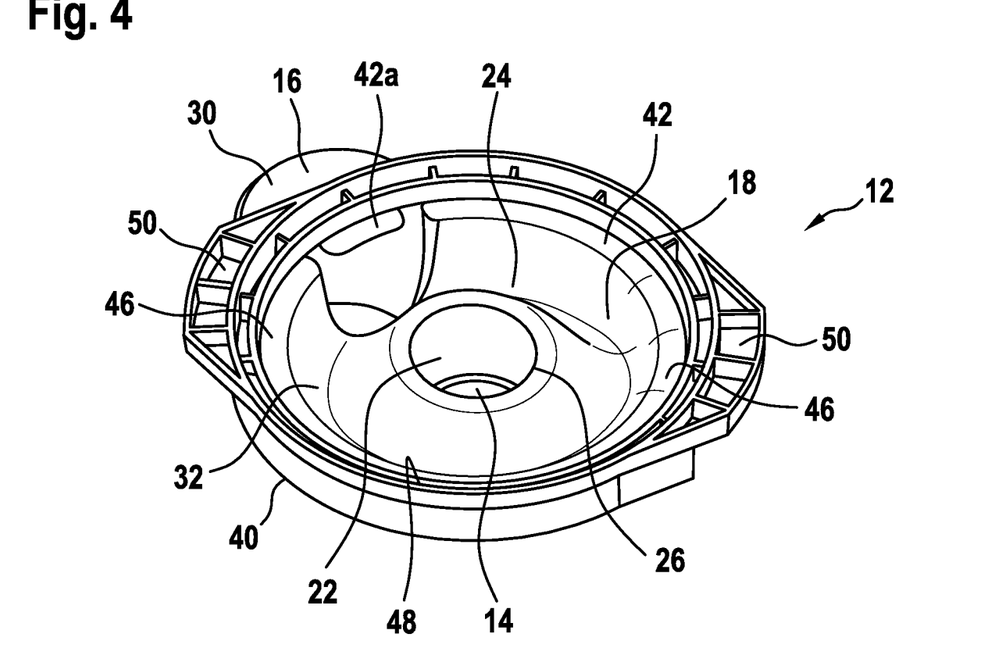
FIG. 4 shows a perspective view of the valve body of the expiratory valve of FIG. 2 from above.

FIG. 2 shows a sectional view of the expiratory valve 10 according to an embodiment, as utilized in FIG. 1. The expiratory valve 10 comprises a valve body 12 having formed therein a fluid inlet 14 and a fluid outlet 16 for breathing air exhaled by a patient. FIGS. 3 and 4 show perspective views of this valve body 12, FIG. 3 showing a view from below approximately from the direction of the arrow designated 12 in FIG. 4, and FIG. 4 showing a view from above approximately from the direction of the arrow designated 12 in FIG. 3. FIG. 2 illustrates the expiratory valve 10 prior to installation in a ventilation device 100 so that the breathing air tube 142 is not yet connected. In the operative state, i.e. after installation of the expiratory valve 10 in a ventilation device 100 according to FIG. 1, the breathing air tube 142 is connected to the fluid inlet 14. Air exhaled by the patient is thus passed to the expiratory valve 10 via the fluid inlet 14. Upon passage through the expiratory valve 10, the exhaled air is sent via the fluid outlet 16 to a surrounding environment of the ventilation device 100.

The expiratory valve 10 comprises a so-called valve plenum 18. The valve plenum 18 defines a cavity which is adapted to be acted upon by fluid (exhaled breathing air) via the fluid inlet 14 and from which fluid (exhaled breathing air) can be discharged via the fluid outlet. Thus, in the valve plenum 18 there is thus formed a fluid flow path between the fluid inlet 14 and the fluid outlet 16 by the valve body 12 and a valve membrane 20. The fluid inlet 14 is designed such that breathing air during exhalation, i.e. during an expiration phase of the ventilation cycle, can enter the valve plenum 18. During an inspiration phase of the ventilation cycle, i.e. when breathing air is supplied to the patient mechanically via the ventilation conduit 130, the fluid inlet 14 is to be closed. To achieve this, there is provided the valve membrane 20 that is associated with the fluid inlet 14. The valve membrane 20 can be displaced at least between a position closing the fluid inlet 14 and a position opening the fluid inlet 14. The valve membrane 20 in particular is designed such that a central portion of the valve membrane 20 abuts the fluid inlet 14 so as to close a fluid entry opening 22 formed at the fluid inlet 14, as long as the pressure on the side of the valve membrane 20 associated with the fluid inlet 14 is not higher by a predetermined pressure than the pressure prevailing on the side of the valve membrane 20 facing away from the fluid inlet 14 (which usually is the ambient pressure). The valve membrane 20 then is in a position closing the fluid inlet 14 or the conduit 140 with respect to the valve plenum 18. This is the position taken by the valve membrane 20 during the inspiration phases. With a sufficiently high positive pressure on its side associated with the fluid inlet 14 or the conduit 140 for exhaled air as compared to the pressure on its side facing away from the fluid inlet 14 or the conduit 140 for exhaled breathing air, the valve membrane 20 moves into a position opening the fluid inlet 14 with respect to the valve plenum 18, so that breathing air from the conduit 140 for exhaled breathing air can flow into the valve plenum 18. This takes place usually during the expiration phases. The valve membrane 20 is made of a plastics material, in particular of a plastics material having elastic properties, for example a silicone or polysiloxane plastics material. The valve membrane 20 may be installed such that it abuts an edge 26 of the fluid inlet 14 surrounding the fluid entry opening 22 in biased manner and without a positive pressure being applied on its side facing the conduit 140 for exhaled breathing air. When a sufficiently large positive pressure is applied to its side facing the conduit 140 for exhaled breathing air, the valve membrane 20 disengages from the edge 26 of the fluid inlet 14 surrounding the fluid entry opening 22, so that exhaled breathing air can flow into valve plenum 18. However, in addition or as an alternative there may also be provided an actuator displacing the valve membrane 20 in a reciprocating manner between the closing position and the opening position. This actuator is driven preferably by the ventilation device and engages, for example, in the central portion of the valve membrane 20 on the side of the valve membrane 20 facing away from the fluid entry opening 22. The respective position of the valve membrane 20 determines the volume of the valve plenum 18 and the fluid flow path formed between the valve membrane 20 and the valve body 12.

The valve body 12 comprises a valve bottom 24 extending on a lower side of the valve plenum 18 from the fluid inlet 14 outwardly so as to reach an outer edge of the valve plenum or the valve bottom. The valve bottom 24, together with the valve membrane 20, defines the fluid flow path formed in the valve plenum 18 between the fluid inlet 14 and the fluid outlet 16. In particular, the valve body 12 in certain embodiments forms a cup-shaped valve plenum 18 which is at least confined in part on its lower side by the valve bottom 24 and into which the fluid inlet 14 opens. The valve bottom 24 in particular can extend in a dish-like manner between the fluid inlet 14 and an outer edge of the valve body 12 (in particular of the valve plenum 18), with the outer edge of the valve bottom 24 constituting at the same time the outer edge of the valve body 12. The fluid inlet 14 then is formed in particular in a central part of the valve bottom 24. The fluid inlet 14 may have in particular a circular cross-sectional area and have an also circular fluid entry surface 22. An edge 26 of the fluid inlet 14 defining the fluid entry surface 22 thus forms an inner edge of the valve bottom 24 which extends starting from the edge 26 on the lower side of the valve plenum 18 to an outer edge of the valve body 12. The outer edge of the valve body 12 in the radial direction is located farthest away from the fluid inlet 14. Thus, the edge 26 does not protrude from the valve bottom—24, at least not abruptly or with a sharp edge, but rather, the valve bottom 24 begins directly at the edge 26 of the fluid entry opening 22 and extends in a smoothly curved contour from this edge 26 outwardly. Due to this configuration, sharp edges are avoided which, when air flows around the same, could cause air stream separation and the generation of noise associated therewith.

The valve bottom 24 has a dish-like configuration. This is to express that the valve bottom 24 extends with a substantially flat, or at the most flat conical, configuration between the inner edge 26 and the outer edge of the same. Possible recesses in the valve bottom 24, for example a groove or channel still to be described in more detail hereinafter, are formed such that an in total rounded and flow-matching contour is created, having various, smoothly merging curvatures.

While the fluid inlet 14 is arranged in a central portion of the valve plenum 18, the fluid outlet 16 is located radially further outside with respect to the fluid inlet 14. In particular, the fluid outlet 16 is arranged at an outer edge of the valve plenum 18. At the location of the valve outlet 16, the valve body 12 is provided, in particular in an outer wall of the valve bottom 24, with an exit opening through which breathing air can flow from the valve plenum 18 to the fluid outlet 16. The exit opening also is provided with edges that are smoothly curved and thus have a configuration that is expedient in terms of flow, so that a flow of breathing air along sharp edges upon discharge from the valve plenum 18 is avoided.

The valve body 12 is made from a plastics material, for example polyethylene, polypropylene or another thermoplastic plastics material. The valve body 12 is an injection-molded part, i.e. it is produced in an injection-molding method. In particular, the valve body 12 may be designed such that it can be manufactured in a single injection-molding process, in particular in the form of a single-component injection-molded part.

The valve body 12 has a fluid inlet portion 28 in which the fluid inlet 14 is formed. The fluid inlet portion 28 in particular is formed integrally with the valve body 12. The fluid inlet portion 28 extends away from the valve bottom 24, in a direction from the lower side of the valve bottom 24 substantially along an axial direction A of the fluid inlet 14. In addition, the fluid inlet portion 28 extends transversely to the valve bottom 24, i.e. it protrudes from a lower side of the valve bottom 24 in the axial direction A of the fluid inlet 14. The axial direction A designates a fluid inlet axis, i.e. an imaginary line in the longitudinal direction of the fluid inlet portion 28 which is located centrally with respect to the fluid inlet 14. With the fluid entry surface 22 being arranged orthogonally with respect to the fluid inlet 14, the fluid inlet axis A extends orthogonally with respect to the fluid entry surface 22 defined by the fluid inlet 14, and is located centrally with respect to the fluid entry surface 22.

The fluid inlet portion 28 forms a first pin-like protrusion that is configured in particular for connecting a breathing air tube, for example the breathing air tube 142 illustrated in FIG. 1. In the variant illustrated in FIG. 2, the first pin-like protrusion has an in particular cylindrical shape. In other modifications, the pin-like protrusion could also be formed so as to slightly taper towards the free end of the same, for example with a slightly conical taper. The first pin-like protrusion may be formed in particular as a pipe fitting having the fluid inlet 14 formed therein.

The valve body 12 moreover defines a fluid outlet portion 30 having the fluid outlet 16 formed therein. The fluid outlet portion 30 in particular may form a second pin-like protrusion which may have a cylindrical or tapering (in particular conical) shape. The second pin-like protrusion may be formed for example as a cylindrical pipe fitting having the fluid outlet 16 formed therein. Also the fluid outlet portion 30 may be formed in particular integrally with the valve body 12. The fluid outlet 16 in particular may have a circular cross-sectional area. The fluid outlet 16 need not necessarily be connected to a further conduit, but may open directly into the surroundings, so that exhaled air is discharged via the fluid outlet 16 to the surrounding environment. The fluid outlet portion 30, on its radially inner side, is connected to the valve plenum 18 via the aforementioned exit opening, so that fluid that has flown into the expiratory valve 10 is passed via the exit opening to the fluid outlet portion 30.

Similar to the fluid inlet portion 28, the fluid outlet portion 30 can also extend in particular from the valve bottom 24, in particular from a lower side of the valve bottom 24. The fluid outlet portion 30 may extend orthogonally with respect to the valve bottom 24 and/or in a direction parallel to the fluid inlet portion 28, as can easily be seen in FIGS. 2 to 4.

The fluid flow path in the valve plenum 18 has a cross-sectional area which, as measured transversely to the fluid flow between the fluid inlet 14 and the fluid outlet 16, is expanding from the fluid inlet 14 towards the fluid outlet 16. This is achieved by a specific configuration and arrangement of the valve body 12, in particular the valve bottom 24 and the valve membrane 20. The valve bottom 24 primarily constitutes a boundary of the fluid flow path on the bottom side. The valve membrane 20 primarily constitutes a boundary of the fluid flow path on the top side of the same. While it is very well possible to make use of a valve membrane 20 similar to conventional valve membranes, the valve bottom 24 is designed such that the cross-sectional area of the fluid flow path increases towards the valve outlet 16. In particular, the valve bottom 24 is designed such that the distance of the same from the valve membrane 20 increases from the fluid inlet 14 towards the fluid outlet 16. This can take place in one or more stages, but in particular takes place continuously from the fluid inlet 14 towards the fluid outlet 16. With the geometry of the expiratory valve 10 illustrated in FIGS. 2 to 4, having the fluid inlet 14 arranged radially inside and centrally and having the fluid outlet 16 arranged radially outside, it is expedient for example to design the fluid flow path such that partial volumes of the fluid flow path with respect to angular portions of equal size each around the fluid inlet 14 change along the circumference of the fluid inlet 14 such that these partial volumes increase in size in the direction towards the fluid outlet 16. Such an effect can be achieved, for example, when a plane along which the valve bottom 24 extends is inclined with respect to a plane along which the valve membrane 20 extends, such that these two planes extend away from each other towards the fluid inlet 16. While for example, the valve membrane 20 will as a rule extend in a plane orthogonal to the fluid inlet axis A (in FIGS. 2 and 3 this plane is illustrated very schematically by broken lines designated C), there may be specific embodiments in which the valve bottom 24 can extend along a plane that is inclined with respect to the fluid inlet axis A at an angle differing from 90 degrees. The plane along which the valve bottom 24 extends is to designate the plane following the central extension of the valve bottom 24, with possible individual (e.g. dent-like) bumps and recesses, respectively, of the valve bottom 24 being disregarded. However, the valve bottom 24 has a continuous recess determining the cross-sectional area of the flow path between the fluid inlet 14 and the fluid outlet 16, as will still be described in the following, so that the plane along which the valve bottom 24 extends, in general, will be determined by the course of this recess (i.e. the course of the deepest locations in the successive cross-sections following the fluid flow path). In FIGS. 2 and 3, the location of this plane is illustrated very schematically by line B. It can be seen that this plane is not parallel to the plane along which valve membrane 20 extends (the latter plane extends orthogonal to the fluid inlet axis A), but rather forms an angle to the fluid inlet axis A that is different from 90 degrees. This implies that the normal vector N of this plane is not parallel to the fluid inlet axis A, but rather forms an angle α with respect to the same. Normally, the normal vector N will be inclined with respect to the fluid inlet axis A towards the fluid outlet 16, as it is also indicated in FIGS. 2 and 3.

The increase in the cross-sectional area of the fluid flow path towards the fluid outlet 16 takes account of the fact that the volume flow of breathing air flowing towards the outlet increases with decreasing distance of the fluid flow path from the fluid outlet. The volume available for the volume flow in the valve plenum 18 thus is matched to the volume flow. Due to such matching of the volume available for the fluid flow, there are avoided stalling effects with resulting swirling of the breathing air to be exhaled.

Moreover, it can readily be seen from FIGS. 2 to 4 that the valve bottom 24 bulges outwardly in an axial direction in a portion around the fluid inlet 14. The expression "bulges outwardly in an axial direction" is to be understood to the effect that the valve bottom 24 has a convex shape at least in a section containing the fluid inlet axis A, namely in a portion between the edge of the fluid inlet 14 and the outer edge of the valve bottom 24. In the embodiments illustrated, this may also be a section in the radial direction. In FIG. 2, this convex shape is illustrated for the section through the deepest location of the thus formed bulge 32 at the fluid outlet 16 on the left side in FIG. 2 and is illustrated for the section through the location of the least depth of the bulge 32 on the right side in FIG. 2. Convex means that, in such a sectional view, a line interconnecting two points on the valve bottom 24 extends through the valve plenum 18. Accordingly, the valve bottom 24, in the region of the bulge 32 thus created, forms a groove or channel extending around the fluid inlet 14 and having a floor bulging in an axial direction between the edge of the fluid inlet 14 and the outer edge of the valve bottom 24. The channel thus defines the fluid flow path around the fluid inlet 14. The respective deepest point of this channel along the fluid flow path (in other words: the connection of the deepest points in respective sections between the fluid inlet 14 and the outer edge of the valve bottom 24) thus forms a line extending around the fluid inlet 14 and designated 34 in FIG. 3. With the radially symmetric geometry of the valve bottom 24 having the fluid inlet 14 in the center, as illustrated in the figures, this line 34 has an elliptical shape due to the differing depth of the channel which still is to be outlined in more detail (the projection of this line 34 onto a plane, such as the plane C, orthogonal to the fluid inlet axis A has a circular shape). As can readily be seen in FIGS. 2 to 4, the bulging portion of the valve bottom 24 (or the channel thus formed) defines two fluid flow paths extending substantially around half of the circumference of the fluid inlet 14, which finally open into the fluid outlet 16 on a lateral side (in FIG. 2 on the left of the fluid inlet 14). In this respect, the bulging portion of the valve bottom 24 has its outer sidewall merging into the fluid outlet portion 30. As was already mentioned, all edges along this fluid flow path are provided with a rounded contour counteracting stalls or air stream separation and/or swirling of the fluid flow.

The figures readily show that the axial bulge 32 of the valve bottom 24 is of varying depth around the circumference of the fluid inlet 14. The depth is to be measured as a distance measured in the direction of the fluid inlet axis A between the valve bottom 24 at the edge 26 of the fluid inlet 14 and the valve bottom 24 at the deepest location of the bulge 32 in a section interconnecting the fluid inlet 14 to the outer edge of the valve bottom 24 (in the case of a radially symmetric geometry of the valve bottom 24 as shown in the figures, this is a radial section through the valve bottom 24). FIGS. 2 and 3 each illustrate the maximum depth Tmax at the location of the fluid outlet 16 and the respective minimum depth Tmin on the side opposite the fluid outlet 16.

Thus, partial volumes of the fluid flow path with respect to respective angular portions of equal size in each case change along the circumference of the fluid inlet 14, such that these partial volumes increase with decreasing distance from the fluid outlet 16. It has shown that this measure contributes quite considerably in reducing flow-caused noise when discharging breathing air during expiration phases as the volume available is matched to the volume flow of the flowing fluid.

The figures also clearly show that the valve bottom 24 has a rounded contour starting from an inside of the fluid inlet 14 at the edge of the fluid entry surface 22 on the side thereof facing the valve plenum 18. This is revealed particularly clearly in FIG. 4. Upon passage of the fluid entry surface 22, the fluid flow flows along the rounded inner edges of the channel formed by the bulge 32 to the deepest location of the same in order to then flow along the fluid flow path formed by the channel following approx. line 34—around the fluid inlet 14 towards the fluid outlet 16. In doing so, the fluid flow passes no sharp edges whatsoever that could cause stalls or swirling along with noise generated thereby.

The valve body 12 furthermore shows reinforcing ribs 36, 38 formed around the fluid inlet 14. In FIGS. 2 and 3 some of these reinforcing ribs are shown in exemplary manner at numerals 36 and 38. The reinforcing ribs 36, 38 reinforce the valve bottom 24, in particular the shell formed by the valve bottom 24 in the bulging portion 32. Torsions of the valve body 22 are effectively suppressed by this additional reinforcement. The reinforcing ribs 36, 38 thus also contribute in reducing the generation of noise as they suppress vibrations of the valve body 24 under the influence of a fluid flow in the valve plenum 18. However, it is also possible to efficiently suppress undesired disturbing vibrations of the valve membrane 20. This reduces the risk for oscillations of the air column in the tube system, which may result in erroneously triggered control operations (in particular so-called auto triggers). The reinforcing ribs 36, 38 are formed integrally with the valve body 12. In this respect, integral is to be understood to the effect that the reinforcing ribs 36, 38 and the valve body 12 are manufactured as one single component part. In the embodiment illustrated, the reinforcing ribs 36, 38 are manufactured in the same injection-molding process as the valve body 12.

The reinforcing ribs 36, 38 are arranged outside of the fluid inlet 14. As can be seen in the figures, they extend outwardly with respect to the edge 26 of the fluid inlet 10, towards the edge of the valve body 12. In the embodiment illustrated, the reinforcing ribs extend in the radial direction with respect to the fluid inlet axis A. However, they may also extend from the inside outwardly in rather spiral fashion. In doing so, the reinforcing ribs connect the edge 26 of the fluid inlet 16 to the outer edge of the valve body 12. The reinforcing ribs 36, 38 are formed on a lower side of the valve bottom 24. Thus, they do not interfere with the fluid flow path formed on the inside of the valve body 12, i.e. on the top side of the valve bottom 24. As can be seen in the figures, the reinforcing ribs comprise first reinforcing ribs 36 and second reinforcing ribs 38. The first reinforcing ribs 36 are inner reinforcing ribs formed between the edge 26 of the fluid inlet 14 and the bulging portion 32 of the valve bottom 24. In the embodiment illustrated, the first reinforcing ribs 36 connect the edge 26 of the fluid inlet 14 to the bulging portion 32 of the valve bottom 24. The second reinforcing ribs 38 are outer reinforcing ribs extending between the bulging portion of the valve bottom 32 and the outer edge of the valve bottom 24. In the embodiment illustrated, the second reinforcing ribs 38 connect the bulging portion 32 of the valve bottom 24 to the outer edge of the valve bottom 24. The second reinforcing ribs 38 terminate in a flange-like shoulder 40 formed at the outer edge of the valve bottom 24. The shoulder 40 may comprise for example at least one step extending around the outer periphery of the valve bottom 24, in particular at least two spaced apart steps, with the second reinforcing ribs 38 merging into the step or an inner one of the steps, respectively. The step or steps may form, for example, a ring-like flange extending around the outer edge of the valve bottom 24 and giving the stability to the same.

As illustrated in FIG. 2, the expiratory valve 10 comprises furthermore the valve membrane 20 associated with the fluid inlet 40. In the state mounted in the expiratory valve 10, the valve membrane 20 has an abutment area thereof, which is formed on the outer edge, resting on the top side of a support 42 which is formed on the top side of the valve body 12. The support 42 forms a projection extending around the outer edge of the valve body 12 and projecting from the outer edge of the valve body 12 inwardly, towards the side of the valve plenum 18. The support 42 is also formed integrally with the valve body 12, for example, in the form of an injection-molded part that is formed in the same injection-molding process as the valve body 12. During assembly of the expiratory valve 10, the valve membrane 20 has its outer abutment area brought into abutting contact with the top side of the support 42 of the valve body 12, so that the valve membrane 20 rests on the edge 26 of the fluid inlet 14 with an abutment area formed in the central part of the same and rests on the support 42 with its abutment area formed in the outer part of the same. The valve membrane 20 thus defines a top side of the fluid flow path formed in the valve plenum 18. The valve membrane 20 then is clamped with respect to the valve body 12 by means of a clamping ring 44 illustrated in FIG. 2. To this end, the clamping ring 44 is placed onto the valve membrane and then is rotated with respect to the valve body 12 in a bayonet-like manner. By way of the clamping forces thus created, the valve membrane 20 is deformed to a certain extent at the periphery of the same.

For this reason, the support 42 has an uneven shape on its top side. The bumps thus formed in the surface of the support 42, which are illustrated in FIG. 4 at numeral 46, compensate the deformation of the valve membrane 20 that is caused when the clamping ring 44 is clamped with respect to the valve body 12, so that the formation of folds or warps at the periphery of the valve membrane 20 in the clamped state can be suppressed. In particular, there are formed bumps 46 on the top side of the support 42 in the form of protuberances or bulges or ribs spaced apart from each other along the circumference. These bulges or ribs may extend radially. It is even better when the bulges or ribs have a thread-like design, i.e. a certain pitch with respect to the plane of the abutting valve membrane 20 and/or do not only extend in the radial direction, but also in the circumferential direction, e.g. extend in a spiral manner around the periphery of the valve body 12. For restricting the clamping forces thus created, it may also be expedient to keep the pitch of the threads formed by the bulges or ribs low and/or to restrict the rising portion, e.g. by a stop at the end of a bulge or rib and/or by a transition into a portion at the end of the bulge or rib extending parallel to the plane of the valve membrane 20. The bumps, in particular in the form of bulges and/or ribs, may be formed integrally with the support 42.

The support 42 may be formed so as to extend continuously around the periphery of the outer edge of the valve body (as shown e.g. by region designated 42 in FIG. 4), or may be formed with interruptions so that individual supporting portions are formed arranged in succession along the circumference of the outer edge of the valve body 12. In the embodiment according to FIG. 4, such an individual supporting portion 42 a is formed on the side of the fluid inlet 16 above the discharge opening between the valve plenum 18 and the fluid outlet 16.

The top side 46 of the support 42 is formed in an uneven manner so that the top side 46 of the support 42 is arranged in an imaginary curved surface, i.e. so that there is no imaginary plane which completely comprises the top side 46 of the support 42. The imaginary curved surface covers a top side of the valve body 12. In particular, it is arranged orthogonally with respect to the fluid inlet axis A constituting at the same time a longitudinal axis of the valve body 12. Due to the uneven shape of the top side 46 of the support 42, a planar surface—when making attempts to place the same on the top side 46 of the support—would not contact the entire top side 46 of the support 42. Rather, there would only be individual locations of the planar surface that establish contact with the top side 46 of the support 42. Thus, at least in the state of the expiratory valve 10 in which the same is not installed in a ventilation device 100, the planar valve membrane 20 does not abut with the entirety of its periphery on the top side 46 of the support 42. Rather, there are individual contact locations between the valve membrane 20 and the support along the periphery of the valve membrane 20. The unevenness of the top side of the support 42 is such that, only when the expiratory valve 10 is installed in the ventilation device 100 and the valve body 12 is subject to stress causing deformation of the same, the top side 46 of the support 42 comes to lie in a planar surface and the valve membrane 20 now has its abutment area in sheet-like or full-area contact with the top side 46 of the support 42.

The valve body 12 comprises at least one mounting lug 50 which is designed for engagement with a bayonet-like expiratory valve connection of a ventilation device 100. The ventilation device then comprises a mating engagement member with which the mounting lug 50 engages upon installation of the expiratory valve 10 so as to retain the expiratory valve 10 to the ventilation device 100. Such a bayonet-type coupling has the property that, upon locking of the expiratory valve 10 to the ventilation device 100, there are created clamping forces slightly deforming the valve body 12.

The valve body 12 comprises at least two mounting lugs 50 associated with each other. The mounting lugs 50 are arranged at the radially outer periphery of the valve body 12 around the circumference of the valve body 12 and project in the radial direction from the respective radially outer edge of the valve body 12 in order to form respective engagement surfaces 52 with a corresponding mating engagement member on the ventilation device 100. When the mounting lugs 50 are engaged with their respective mating engagement members provided on the ventilation device 100, the valve body 12, on the respective sides thereof provided with the mounting lugs 50, will be moved towards the ventilation device 100. In the course of this forced movement, there is stress created in the valve body 12, and the upper edge 48 of the valve body 12 bends towards the ventilation device 100 on the sides thereof on which the mounting lugs 50 are disposed. The uneven design of the top side 46 of the support 42 provided on the valve body 12 for the valve membrane 20 is intended to compensate this bending of the valve body 12. When the mounting lugs 50 are brought into engagement with the respective mating engagement member on the ventilation device 100, the top side 46 of the support 42 is to be flat, i.e. is to be arranged in a plane. The two mounting lugs 50 are arranged opposite each other at an angle of 180°, i.e. are arranged on opposite sides of the valve body 12 across the valve plenum 18.

The top side 46 of the support 42 is located in an outwardly curved imaginary surface with respect to the valve plenum 18, which covers the top side of the valve body 12. In particular, the outwardly curved imaginary surface, with respect to the valve plenum 18, is located further outside than an imaginary plane through at least two different points on the top side 46 of the support 42 on sides where the mounting lugs 50 are present (i.e. on the left and right sides in FIG. 4). The top side 46 of the support 42 is located in a convexly curved imaginary surface so that a line connecting two points in the imaginary surface extends through the valve plenum 18. The top side 46 of the support 42 bulges outwardly starting from the two mounting lugs 50. At the locations where the mounting lugs 50 are provided, the top side 46 of the support 42 does not at all bulge outwardly, whereas it has its maximum outward bulge in the middle between the two mounting lugs 50 (in FIG. 4 along a line in vertical direction orthogonally to a connection between the two mounting lugs 50). This takes account of the fact that the deformation of the valve body 12, upon mounting of the expiratory valve 10 to the ventilation device 100, is strongest at the locations where the mounting lugs 50 are provided. At this location, the upper edge 48 of the valve body 12 is bent upwardly most strongly.

In the embodiment illustrated, the curved imaginary surface is a lateral surface of a cylinder, with the axis of the cylinder being orthogonal to a connecting line between the two associated mounting lugs 50.

Due to the stress applied during mounting of the expiratory valve 10 to the valve body 12 at the locations where the mounting lugs 50 are present, the upper edge 48 of the valve body 12 also bends in the same manner at these locations towards a counter side on the ventilation device 100. For compensation of this effect, it is expedient to form also the valve body 12, or more strictly speaking the upper edge 48 of the valve body 12, in a corresponding manner to the support 42 for the valve membrane 20. The upper edge 48 of the valve body 12, upon mounting of the expiratory valve 10 to the ventilation device 100, is to abut on a counter surface of the ventilation device 100 across an as large an area as possible in order to ensure an as tight as possible abutment of the valve membrane 20. To this end, the valve body 12 has an upper edge 48 which is arranged in an outwardly curved imaginary surface with respect to the valve plenum 18. The considerations given hereinbefore for the top side 46 of the support 42 apply analogously to the design of the upper edge 48 of the valve body 12. In particular, the upper edge 48 of the valve body 12 is arranged in a convexly curved imaginary surface with respect to valve plenum 18 and bulges outwardly from the at least one mounting lug 50. The bulge of the upper edge 48 of the valve body 12 is larger in a region located between the two mounting lugs 50 than in a region adjacent one of the two mounting lugs 50.

The uneven shape of the top side 46 of the support 42 and the uneven shape of the upper edge 48 of the valve body 12 are matched with respect to each other. This makes sense as the effect to be achieved for both of the same is that, upon mounting of the expiratory valve 10 to the ventilation device 100, both the top side 46 of the support 42 and the upper edge 48 of the valve body 12 are arranged in a planar surface. In particular, the top side 46 of the support 42 as well as the upper edge 48 of the valve body 12 are bulging outwardly in a mutually aligned manner, with the locations of minimum bulge and maximum bulge being matched to each other, and in particular are arranged at the same location with respect to a plane covering the valve plenum 18. The design is even such that the top side 46 of the support 42 and the upper edge 48 of the valve body 12 have approx. the same bulge and in particular are arranged in mutually parallel imaginary surfaces.

Each of the mounting lugs 50 has an engagement surface 52 for engagement with a mating engagement member provided on the ventilation device 100, with the engagement surface 52 being provided with a lead-in chamfer 52a that is matched with respect to the bulge of the top side of the support 42. As is usual with a bayonet-type engagement, the engagement surface 52 as a rule will be formed substantially parallel to an upper edge of the mounting lug. In the front portion thereof, there is provided the lead-in chamfer 52 a. In the region of the lead-in chamfer 52 a, the engagement surface 52 then extends at an angle, in particular an acute angle, with respect to the upper edge of the mounting lug 50. The angle is selected such that a thickness between engagement surface 52 and upper edge of the mounting lug 50 increases with increasing distance from the beginning of the engagement surface 52. This permits a certain extent of stress to be created upon engaging the mounting lug 50 with the mating engagement member on ventilation device 100, which promotes a certain force-fit or frictional engagement and thus a firm and safe seating arrangement of the expiratory valve 10 on the ventilation device 100. The lead-in chamfer 52 a is designed such that a bias is created when the mounting lug 50 is clamped to the ventilation device 100, with said bias acting on the upper edge 48 of the valve body on the side of the mounting lug 50. This is accompanied by a certain deformation of the valve body 12 on the side facing the mounting lug 50 with respect to sides or locations remote from the mounting lug 50. In particular, the upper edge 48 of the valve body 12, by movement of the mating engagement member along the lead-in chamfer 52 a, is brought closer to the ventilation device 100. On the other hand, locations remote from the mounting lug 50 already abut a contact area of the ventilation device 100 and cannot get closer. As a result, there is created a deformation of the upper edge 48 of the valve body 12, with the deformation becoming increasingly stronger towards the mounting lug 50. This effects a bias in the valve body 12 which increases with increasing movement of the mating engagement member along the lead-in chamfer 52 a. The lead-in chamfer 52 a is selected such that, upon clamping, a bias is generated that is just sufficiently large to make the upper edge 48 of the valve body 12 planar in the clamped state, i.e. that the upper edge 48 of the valve body 12 in the clamped state is located in a plane covering the valve plenum 18. The upper edge 48 of the valve body 12 then is in sheet-like contact with a counter surface of the ventilation device 100. The support 42 for the valve membrane 20, which is formed integrally with the valve body 12, is equally bent. For permitting the top side 46 of this support 42 to be planar as well in the state of the expiratory valve 10 mounted to the ventilation device 100, it is expedient when the top side 46 of the support 42 is uneven to the same extent as the upper edge 48 of the valve body 12. Accordingly, the lead-in chamfer 52 a of the mounting lug 50 is matched to the bulge of the support 42.

For being able to define the end of the lead-in chamfer 52 a as well as possible and to thus allow the bias for the valve body 12 to be adjusted as accurately as possible, it may be provided that the engagement surface 52 has a non-tapering portion 52 b following the lead-in chamfer 52 a. In the non-tapering portion 52 b, the engagement surface 52 is parallel to the upper edge of the mounting lug 50. A bias and bending of the valve body 12 once reached thus does not change any more when the counter engagement member reaches the non-tapering portion 52 b. The bias and bending can thus be adjusted in a well reproducible manner, as it is no longer of great relevance which location of the non-tapering portion 52 b is reached by the mounting lug 50. Moreover, the engagement surface 52 is provided with a stop 54 at the end thereof, which defines an end of the engagement movement between mounting lugs 50 and ventilation device 100.

The expiratory valve 10 described can be designed as a single-use component, i.e. in the form that it can be used only once and has to be disposed of after use. Such expiratory valves are inexpensive in manufacture and nevertheless fulfill the required hygiene standards. As an alternative the expiratory valve 10 may also be designed to permit multiple use. To this end, the design of the expiratory valve 10 would have to be such that it can be disinfected after use, for example by autoclaving. The expiratory valve then needs to be designed to withstand autoclaving.

The invention claimed is:

1. An expiratory valve of a ventilation device, comprising
   a valve body having a fluid inlet, a fluid outlet for breathing air of a patient formed therein, said valve body having at least one reinforcing rib formed around the fluid inlet;
   wherein the at least one reinforcing rib extends outwardly in a radial direction with respect to a center of a cross-sectional area of the fluid inlet;
   wherein the valve body forms a cup-shaped valve plenum into which the fluid inlet opens;
   wherein the fluid inlet is disposed in a central portion of the valve plenum;
   wherein the valve body forms a valve bottom which at least partly encloses the valve plenum, said valve bottom extending in a dish-like manner between the fluid inlet and an outer edge of the valve plenum;
   wherein the valve bottom extends in a flat or flat conical manner between the fluid inlet and an outer edge; and
   wherein the at least one reinforcing rib comprises a first reinforcing rib extending outwardly from the edge of the fluid inlet along the valve bottom;
   wherein the first reinforcing rib forms an inner reinforcing rib extending outwardly from the edge of the fluid inlet to an axial bulging portion of the valve bottom, and a second reinforcing rib and a third reinforcing rib form outer reinforcing ribs extending outwardly from the axial bulging portion to the outer edge of the valve bottom.

2. The expiratory valve of claim 1,
   wherein the valve body is made of plastics material.

3. The expiratory valve of claim 2,
   wherein the valve body is an injection-molded part.

4. The expiratory valve of claim 1,
   wherein the at least one reinforcing rib is formed integrally with said valve body.

5. The expiratory valve of claim 1,
wherein the at least one reinforcing rib extends outwardly with respect to an edge of the fluid inlet.

6. The expiratory valve of claim 1,
wherein the valve body has a fluid inlet portion having the fluid inlet formed therein.

7. The expiratory valve of claim 6,
wherein the fluid inlet portion forms a first pin-like protrusion.

8. The expiratory valve of claim 1,
wherein the fluid outlet is disposed further outside in the radial direction with respect to the fluid inlet.

9. The expiratory valve of claim 1,
wherein the valve bottom originates from an edge of the fluid inlet defining a fluid entry surface.

10. The expiratory valve of claim 9,
wherein the valve bottom, starting from an inside of the fluid inlet at the edge of the fluid entry surface, has a rounded contour on its side facing the valve plenum.

11. The expiratory valve of claim 1,
wherein the valve bottom defines a fluid flow path between the fluid inlet and the fluid outlet, with the cross-sectional area of said fluid flow path expanding towards the fluid outlet.

12. The expiratory valve of claim 11,
wherein the axial bulging portion has a varying depth around the circumference of the fluid inlet.

13. The expiratory valve of claim 12,
wherein the depth of the bulge increases in circumferential direction towards the fluid outlet.

14. The expiratory valve of claim 12,
wherein the depth of the bulge in circumferential direction is smallest on a side opposite the fluid outlet.

15. The expiratory valve of claim 12,
wherein the depth of the bulge in circumferential direction is largest on the side towards the fluid outlet.

16. The expiratory valve of claim 1,
wherein the valve body defines a fluid outlet portion having the fluid outlet formed therein.

17. The expiratory valve of claim 16,
wherein a bulging portion of the valve bottom merges into the fluid outlet portion.

18. The expiratory valve of claim 1,
further comprising a valve membrane associated with the fluid inlet, which is displaceable at least between a position closing the fluid inlet and a position opening the fluid inlet.

19. The expiratory valve of claim 18,
wherein the valve body further comprises a support onto the top side of which the valve membrane can be placed with an abutment area formed at the outer edge thereof, wherein the support has an uneven design on its top side.

20. A ventilation device, comprising an expiratory valve according to claim 1 that is adapted to be connected to an expiration air conduit.

* * * * *